US00PP26238P2

(12) United States Plant Patent
de Groot

(10) Patent No.: US PP26,238 P2
(45) Date of Patent: Dec. 15, 2015

(54) ***HYPERICUM* PLANT NAMED 'RUIHYG207B'**

(50) Latin Name: *Hypericum×inodorum*
Varietal Denomination: Ruihyg207b

(71) Applicant: Henk C. A. de Groot, Amstelveen (NL)

(72) Inventor: Henk C. A. de Groot, Amstelveen (NL)

( * ) Notice: Subject to any disclaimer, the term of this patent is extended or adjusted under 35 U.S.C. 154(b) by 108 days.

(21) Appl. No.: 13/998,757

(22) Filed: Dec. 3, 2013

(51) Int. Cl.
*A01H 5/02* (2006.01)

(52) U.S. Cl.
USPC ..... Plt./442

(58) Field of Classification Search
USPC ..... Plt./442, 263.1, 226
CPC ..... A01H 5/02; A01H 5/00
See application file for complete search history.

(56) References Cited

PUBLICATIONS http://taspo.de/aktuell/alle-news/detail/beitrag/20092-neue-sorten-neuheiten-trio-bei-hypearl-hypericum.html 10 pages, 2011.*

* cited by examiner

*Primary Examiner* — Kent L Bell
(74) *Attorney, Agent, or Firm* — Penny J. Aguirre

(57) ABSTRACT

A new cultivar of *Hypericum×inodorum*, 'Ruihyg207b', that is characterized by its compact plant habit suitable for container growing, its medium sized berries that are red in color and oval in shape, and its small sized, light green sepals that are ovate in shape.

2 Drawing Sheets

Botanical classification: *Hypericum×inodorum.*
Variety denomination: 'Ruihyg207b'.

BACKGROUND OF THE INVENTION

The present invention relates to a new and distinct cultivar of *Hypericum×inodorum* and will be referred to hereafter by its cultivar name, 'Ruihyg207b'. 'Ruihyg207b' is a semi-evergreen shrub grown for use as a landscape plant and container plantings.

The new cultivar was derived from a controlled breeding program conducted by the Inventor in Hazerswoude, The Netherlands. The overall purpose of the breeding program was to develop new cultivars of *Hypericum* plants with unique berries and improved resistance to *Melampsora hypericorum.*

The new cultivar arose from a cross made by the Inventor in Hazerswoude, The Netherlands in April 2006 between an unnamed plant from the Inventor's breeding program, designated 'Hp-03-0019-145', as the female parent and 'Annelies Hypearl' (not patented) as the male parent. The Inventor selected 'Ruihyg207b' as a single unique plant amongst the seedlings that resulted from the above cross in autumn of 2007.

Asexual propagation of the new cultivar was first accomplished by the Inventor by vegetative stem cuttings in 2009 in Hazerswoude, The Netherlands. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ruihyg207b' as a unique cultivar of *Hypericum.*

1. 'Ruihyg207b' exhibits a compact plant habit suitable for container growing.
2. 'Ruihyg207b' exhibits medium sized berries that are red in color and oval in shape.
3. 'Ruihyg207b' exhibits small sized, light green sepals that are ovate in shape.

The female parent of 'Ruihyg207b', 'Hp-03-0019-145', differs from 'Ruihyg207b' in having berries that are light red in color and rounded in shape. The male parent of 'Ruihyg207b', 'Annelies Hypearl', differs from 'Ruihyg207b' in having berries that are green in color. 'Ruihyg207b' can be most closely compared to the cultivar 'Hot Hypearl' (not patented). 'Hot Hypearl' differs from 'Ruihyg207b' in having berries that are slightly darker in color and more rounded in shape.

BRIEF DESCRIPTION OF THE DRAWINGS

The accompanying colored photographs illustrate the overall appearance and distinct characteristics of the new *Hypericum*. The plants in the photographs were taken of plants two years in age as grown in a one-gallon container in a greenhouse in Lelystad, The Netherlands.

The photograph in FIG. 1 provides a side view of 'Ruihyg207b' in bloom.

Figure 1:
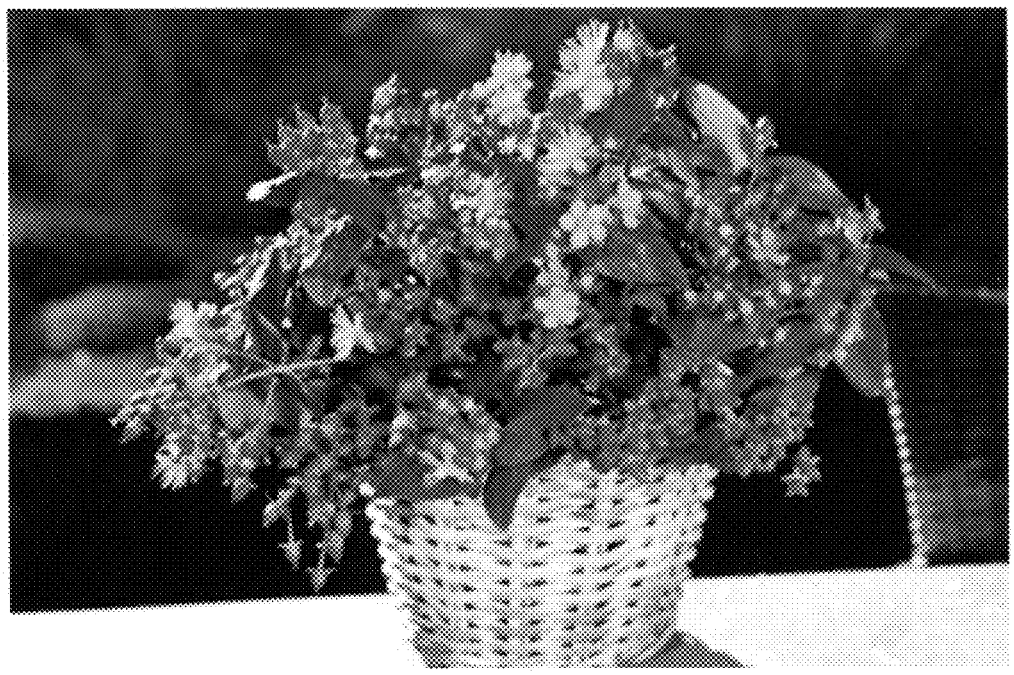
Figure 2:
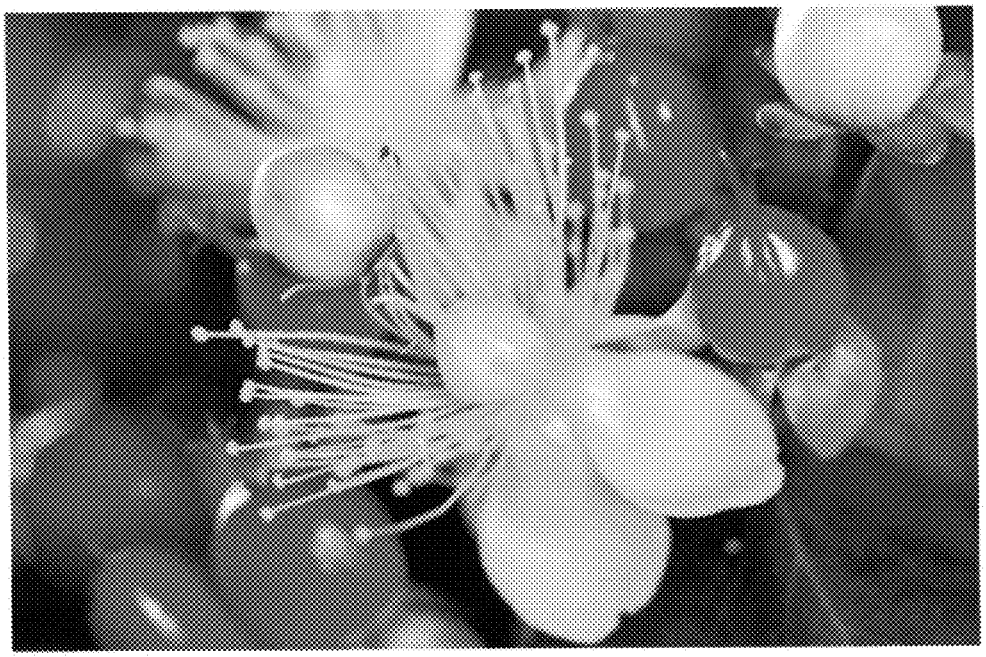

The photograph in FIG. 2 provides a close-up view of a flower of 'Ruihyg207b'.

Figure 3:
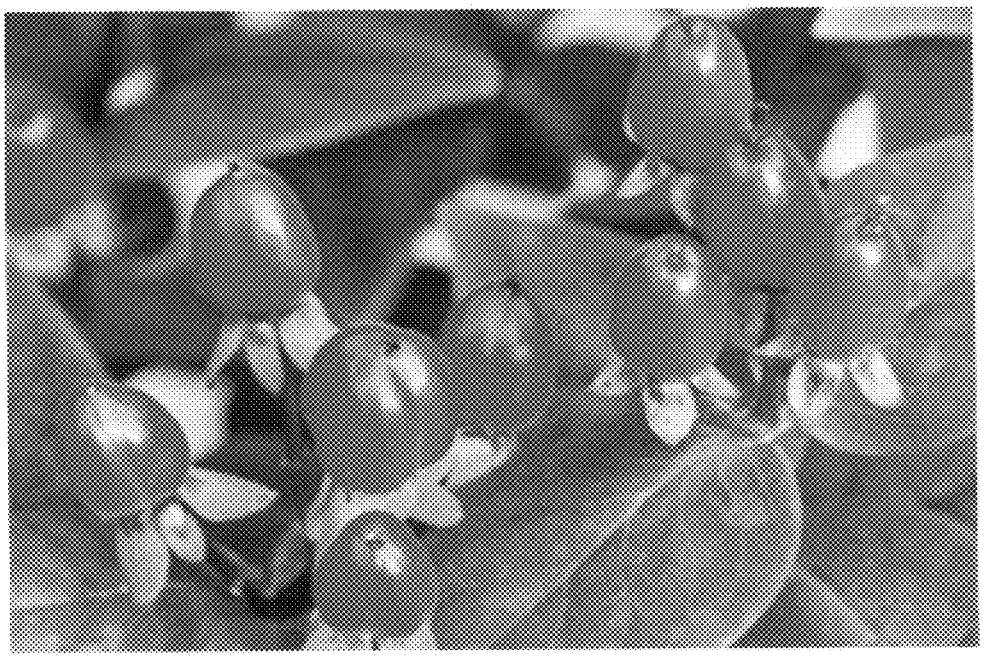

The photograph in FIG. 3 provides a close-up view of the berries of 'Ruihyg207b'.

The colors in the photographs are as close as possible with the digital photography techniques available and the color values cited in the detailed botanical description accurately describe the colors of the new *Hypericum.*

DETAILED BOTANICAL DESCRIPTION

The following is a detailed description of two year-old plants of the new cultivar as grown outdoors in 2-gallon containers in Davidsonville, Md. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July to September in The Netherlands.

*Plant type*.—Semi-evergreen shrub.

*Plant habit*.—Compact with suitability for container growing.

*Height and spread*.—Reaches an average of 40 cm in height and spread.

*Cold hardiness*.—Observed to be hardy to at least −10° C.

*Diseases*.—Has shown tolerance to *Melampsora hypericorum*.

*Root description*.—Fibrous and fine.

*Propagation*.—Vegetative stem cuttings.

*Growth rate*.—Moderate, typical for cultivars of *Hypericum×inodorum*.

Stem description:

*Shape*.—Round.

*Stem color*.—New growth; 145A suffused with 184A to 184C, maturing branches become 166A to 166C as they become woody.

*Stem size*.—Main stems; an average of 35 cm in length and 6 mm in width, lateral branches; an average of 25 cm in length and 5 mm in width.

*Stem surface*.—Glabrous.

*Internode length*.—Average of 5.2 cm.

*Branching*.—Moderately branched with lateral branches upright to an average of 10° angle from vertical.

Foliage description:

*Leaf shape*.—Lanceolate to ovate.

*Leaf division*.—Simple.

*Leaf base*.—Cordate to truncate.

*Leaf apex*.—Acute.

*Leaf fragrance*.—None.

*Leaf venation*.—Pinnate, not conspicuous, 139A on upper surface and 139C on lower surface.

*Leaf margins*.—Entire and undulate.

*Leaf arrangement*.—Opposite, aspect is horizontal to slightly upward.

*Leaf attachment*.—Sessile.

*Leaf substance*.—Moderate.

*Leaf surface*.—Glabrous on upper and lower surface.

*Leaf size*.—An average of 7 cm in length, an average of 4.6 cm in width.

*Leaf color*.—Newly expanded leaves; upper surface a blend of 144A and 143A, lower surface 144A to 144B, mature leaves; upper surface 139A, lower surface 139C.

Inflorescence description:

*Inflorescence type*.—Terminal compound corymb.

*Flower buds*.—Globose in shape with rounded apex, an average of 5 mm in length and width, calyx portion is wrapped around petals and 143A in color suffused with 58A at the base, petal portion is 7A in color.

*Flower fragrance*.—None detected.

*Flower quantity*.—An average of 9 per lateral branch.

*Flower type*.—Complete, rotate with reflexed petals and prominent stamens and ovary.

*Flower aspect*.—Upward facing.

*Flower lastingness*.—About 5 days.

*Flower size*.—Average of 2.5 cm in diameter and 1.3 cm in depth.

*Petals*.—5, elliptic to oblanceolate in shape, un-fused, curved inward and becoming horizontal, upper surface is glabrous and lower surface is satiny, entire margin, truncate base, rounded apex with single slight notched, an average of 1.3 cm in length and 7 mm in width, color upper surface 14A, color lower surface 9B.

*Calyx*.—Reflexed, un-fused sepals, about 1.4 cm in diameter and 3 mm in depth.

*Sepals*.—5, oblong to ovate in shape, 143A in color suffused with 58A near the base on upper surface and 143B in color suffused with 58A near the base on lower surface, glabrous on upper and lower surface, an average of 7 mm in length and 5 mm in width, entire margin, round-truncate base, acute-attenuate apex.

*Peduncles*.—An average of 1 cm in length and 2 mm in width, 144A in color, glabrous surface.

*Pedicels*.—An average of 2 cm in length and 1 mm in width, 144A suffused with 58A in color, glabrous surface.

Reproductive organs:

*Gynoecium*.—Compound pistil about 8 mm in length and 5 mm in width, styles; 3, 4B in color and about 3 mm in length and 0.5 mm in width, stigmas; 3, 21A in color an average of 1 mm in diameter, ovary is superior and 4C in color, an average of 6 mm in length and 4 mm in width.

*Androecium*.—Numerous stamens (an average of 100), spreading outward from base of ovary extending about 1.5 cm in diameter, filaments are 7A in color, an average of 1 cm in length and 0.2 mm in width, anthers are 14A in color, dorsifixed, an average of 1 mm in length and width, pollen was not visible.

*Fruit*.—Conical in shape with mucronate apex, glabrous and satiny surface, an average of 1.4 cm in length and 9 mm in width, 58B in color and 157D at base, fruit color transitions to a blend of N187A and 200A with a dried raisin like appearance with age.

It is claimed:

1. A new and distinct cultivar of *Hypericum* plant named 'Ruihyg207b' as herein illustrated and described.

* * * * *